US005744660A

United States Patent [19]
Bradley et al.

[11] Patent Number: 5,744,660
[45] Date of Patent: Apr. 28, 1998

[54] PRODUCTS OF TETRAFLUOROTHANES

[75] Inventors: Lisa Bradley, Waterloo; Leslie Burgess, Runcorn; Richard Llewellwyn Powell, Tarporley; Geoffrey James Moore, Northwich; Paul Nicholas Ewing, Stockton Heath; Kenneth Taylor, Great Sankey, all of England

[73] Assignee: Imperial Chemical Industries PLC, London, England

[21] Appl. No.: 576,049

[22] Filed: Dec. 21, 1995

Related U.S. Application Data

[63] Continuation of Ser. No. 190,191, filed as PCT/GB93/01208, Jun. 8, 1993, abandoned.

[30] Foreign Application Priority Data

| Jun. 10, 1992 | [GB] | United Kingdom | 9212251 |
| Jun. 10, 1992 | [GB] | United Kingdom | 9212328 |
| Jun. 10, 1992 | [GB] | United Kingdom | 9212330 |
| Aug. 24, 1992 | [GB] | United Kingdom | 9217965 |
| Aug. 24, 1992 | [GB] | United Kingdom | 9217966 |

[51] Int. Cl.$^6$ ................................. C07C 17/08

[52] U.S. Cl. .................. 570/169; 570/151; 570/166; 570/167; 570/168

[58] Field of Search .................. 570/151, 166, 570/167, 168, 169

[56] References Cited

U.S. PATENT DOCUMENTS

| 4,158,675 | 6/1979 | Potter | 570/166 |
| 4,851,595 | 7/1989 | Gumprecht . | |
| 4,950,815 | 8/1990 | Moore et al. | 570/151 |
| 5,185,482 | 2/1993 | Manzer | 570/166 |

FOREIGN PATENT DOCUMENTS

| A 0331991 | 9/1989 | European Pat. Off. . |
| A 0365296 | 4/1990 | European Pat. Off. . |
| A 0408005 | 1/1991 | European Pat. Off. . |
| A 0449617 | 10/1991 | European Pat. Off. . |
| 1000083 | 8/1965 | United Kingdom . |
| 1578933 | 11/1980 | United Kingdom . |

Primary Examiner—Alan Siegel
Attorney, Agent, or Firm—Pillsbury Madison & Sutro LLP

[57] ABSTRACT

This invention relates to a process for the production of 1,1,2,2- and/or 1,1,1,2-tetrafluoroethanes, and in particular to a process for the production of 1,1,1,2-tetrafluoroethane.

10 Claims, No Drawings

PRODUCTS OF TETRAFLUOROTHANES

This is a continuation of application Ser. No. 08/190,191, filed on Jun. 6, 1994, which is a Section 371 filing based on PCT/GB93/01208, filed Jun. 8, 1993, which was abandoned upon the filing hereof.

BACKGROUND OF THE INVENTION

Processes have been proposed for the production of 1,1,1,2-tetrafluoroethane, otherwise known as HFA 134a, which is employed as a replacement for chlorofluorocarbons, in particular dichlorodifluoromethane, in the many applications in which chlorofluorocarbons are employed.

Thus it has been proposed in United Kingdom Patent Specification No. 1,589,924 to produce HFA 134a by the vapour phase fluorination of 1,1,1-trifluoro-2-chloroethane (HCFC 133a) which is itself obtainable by the fluorination of trichloroethylene as described in United Kingdom Patent Specification No. 1,307,224.

The formation of HFA 134a as a minor product of the fluorination of trichloroethylene is described in United Kingdom Patent Specification No 819,849, the major reaction product being HCFC 133a.

More recently, processes for the production of HFA 134a from trichloroethylene based on a combination of the reaction of trichloroethylene with hydrogen fluoride to produce HFA 133a and the reaction of HFA 133a with hydrogen fluoride to produce HFA 134a have been proposed.

In WO 90/08755, the contents of which are incorporated herein by reference, there is described the conversion of trichloroethylene to HFA 134a wherein the two reactions steps are carried out in a single reaction zone with recycle of part of the product stream; a process referred to hereinafter as the "one pot" process.

In EP 0 449 614, the contents of which are also incorporated herein by reference, there is described a process for the manufacture of HFA 134a which comprises the steps of:

(A) contacting a mixture of trichloroethylene and hydrogen fluoride with a fluorination catalyst under superatmospheric pressure at a temperature in the range from about 200° C. to about 400° C. in a first reaction zone to form a product containing 1,1,1-trifluoro-2-chloroethane and hydrogen chloride together with unreacted starting materials, (B) passing product of step A together with hydrogen fluoride to a second reaction zone containing a fluorination catalyst at a temperature in the range from about 280° C. to about 450° C. but higher than the temperature in step A to form a product containing 1,1,1-trifluoro-2-chloroethane, 1,1,1,2-tetrafluoroethane and hydrogen chloride, (C) treating product of step B to separate 1,1,1,2-tetrafluoroethane and hydrogen chloride from 1,1,1-trifluoro-2-chloroethane, and unreacted hydrogen fluoride, and (D) feeding 1,1,1-trifluoro-2-chloroethane obtained from step C together with trichloroethylene and hydrogen fluoride to said first reaction zone (step A).

In EP 0 449 617, the contents of which are also incorporated herein by reference, there is described a process for the production of HFA 134a which comprises the steps of:

(A) contacting a mixture of 1,1,1-trifluoro-2-chloroethane and hydrogen fluoride with a fluorination catalyst at a temperature in the range from about 280° C. to about 450° C. in a first reaction zone to form a product containing 1,1,1,2-tetrafluoroethane and hydrogen chloride together with unreacted starting materials, (B) passing product of step A together with trichloroethylene to a second reaction zone containing a fluorination catalyst at a temperature in the range from about 200° C. to about 400° C. but lower than the temperature in step A to form a product containing 1,1,1-trifluoro-2-chloroethane, 1,1,1,2-tetrafluoroethane, hydrogen chloride and unreacted trichloroethylene and hydrogen fluoride, (C) treating product of step B to separate 1,1,1,2-tetrafluoroethane and hydrogen chloride from 1,1,1-trifluoro-2-chloroethane, unreacted trichloroethylene and hydrogen fluoride, and (D) feeding 1,1,1-trifluoro-2-chloroethane obtained from step C together with hydrogen fluoride to said first reaction zone (step A).

SUMMARY OF THE INVENTION

We have now found that 1,1,2,2-tetrafluoroethane and 1,1,1,2-tetrafluoroethane isomers, but in particular the 1,1,2,2-tetrafluoroethane isomer may be produced by the fluorination of 1,1,2,2-tetrachloroethane by contacting 1,1,2,2-tetrachloroethane with hydrogen fluoride in the liquid phase in the presence of a fluorination agent/catalyst or in the vapour phase at temperatures in the range from about 200° C. to about 400° C. in the presence of a fluorination catalyst whereby to produce tetrafluoroethanes.

Suitable catalysts are those which yield tetrafluoroethanes as a product of the reaction with a yield of greater than 10%, preferably greater than 20% and more preferably greater than 25%, based on the 1,1,2,2-tetrachloroethane processed. Suitable fluorination catalysts for use in vapour phase processes include catalysts based on chromia or chromium oxyfluoride, and the fluorides or oxyfluorides of other metals, for example magnesium and aluminium. Activity promoting amounts of other metals, for example zinc and nickel may also be present. Suitable catalysts/agents for use in liquid phase processes include antimony pentafluoride and titanium tetrafluoride; these may act as reagents or catalysts or both.

1,1,2,2-tetrafluoroethane produced by the present processes may be isomerised to 1,1,1,2-tetrafluoroethane; suitable conditions are described for example in European Patent Publication No 0 365 296, the contents of which are incorporated herein by reference.

The relative proportion of hydrogen fluoride to 1,1,2,2-tetrachloroethane which is employed may vary within wide limits although it is generally preferred to employ a stoichiometric excess of hydrogen fluoride. The stoichiometrically required molar ratio is 4:1. The proportion of hydrogen fluoride to 1,1,2,2-tetrachloroethane may therefore be at least 4:1, preferably at least 6:1 and substantially greater excesses of hydrogen fluoride, for example up to 50:1, may be employed if desired.

In the case of a liquid-phase process, the fuorination of the 1,1,2,2-tetrafluoroethane may be carried out under any conditions of temperature and pressure under which the tetrachloroethane is in the liquid phase. Usually, depending upon the pressure, the process will be carried out at below 200° C. for example at about room temperature to 100° C. Preferably the conditions of temperature and pressure are chosen such that the 1,1,2,2-tetrachloroethane is in the liquid phase whilst the product(s), 1,1,2,2-tetrafluoroethane and/or 1,1,1,2-tetrafluoroethane are in the vapour phase Vapour-phase processes are preferred, in which case the temperature at which the process is carried out is preferably at least 250° C., more preferably at least 260° C. and is preferably not greater than 350° C.

One by-product of the vapour-phase process is trichloroethylene which results from a competing elimination reaction, that is the elimination of HCl from 1,1,2,2-tetrachloroethane. Whilst trichloroethylene can be fluorinated under the reaction conditions to 2-chloro-1,1,1-trifluoroethane which can itself be fluorinated to 1,1,1,2-tetrafluoroethane, this route to 1,1,1,2-tetrafluoroethane is equilibrium limited and the formation of trichloroethylene is desirably suppressed.

In order to suppress any decomposition of the 1,1,2,2-tetrachloroethane to trichloroethylene the 1,1,2,2-tetrachloroethane is preferably maintained prior to feeding it to the reactor in which the process of the invention is effected at a temperature below that at which the process of the present invention is effected, the 1,1,2,2-tetrachloroethane feed then being passed through a vaporiser as late as possible before being fed to the reactor. In addition, the amount of trichloroethylene produced by decomposition of the 1,1,2,2-tetrachloroethane to trichloroethylene may further be suppressed by co-feeding hydrogen fluoride or hydrogen chloride with the 1,1,2,2-tetrachloroethane vapour feed.

Free-radical inhibitors may also be added to the 1,1,2,2-tetrachloroethane feed in order to prevent any undesirable premature decomposition of the 1,1,2,2-tetrachloroethane. Suitable free-radical inhibitors will be readily apparent and any suitable inhibitor may be employed; as examples of suitable inhibitors may be mentioned As described previously, hydrofluorination of trichloroethylene is used for the production of 1,1,1,2-tetrafluoroethane. If desired the process of the invention may be combined with processes for the production of 1,1,1,2-tetrafluoroethane based on trichloroethylene; thus and according to a preferred embodiment of the invention, 1,1,2,2-tetrachloroethane is fed, as a second starting material to processes for the production of 1,1,1,2-tetrafluoroethane employing trichloroethylene as the starting material. An advantage of this preferred embodiment of the invention resides in the discovery that co-feeding trichloroethylene and 1,1,2,2-tetrachloroethane has the effect of suppressing the amount of trichloroethylene produced by the elimination of hydrogen chloride from the 1,1,2,2-tetrachloroethane.

The co-feeding of trichloroethylene and 1,1,2,2-tetrachloroethane may be effected in the processes described in our published European Applications No. 0 449 617, and No 0 449 614 the contents of which are incorporated herein by reference.

The process described in EP 449,617 is for the production of 1,1,1,2-tetrafluoroethane (HFA 134a) which comprises the steps of:

(A) contacting a mixture of 1,1,1-trifluoro-2-chloroethane and hydrogen fluoride with a fluorination catalyst at a temperature in the range from about 280° C. to about 450° C. in a first reaction zone to form a product containing 1,1,1,2-tetrafluoroethane and hydrogen chloride together with unreacted starting materials, (B) passing product of step A together with trichloroethylene to a second reaction zone containing a fluorination catalyst at a temperature in the range from about 200° C. to about 400° C. but lower than the temperature in step A to form a product containing 1,1,1-trifluoro-2-chloroethane, 1,1,1,2-tetrafluoroethane, hydrogen chloride and unreacted trichloroethylene and hydrogen fluoride, (C) treating product of step B to separate 1,1,1,2-tetrafluoroethane and hydrogen chloride from 1,1,1-trifluoro-2-chloroethane, unreacted trichloroethylene and hydrogen fluoride, and (D) feeding 1,1,1-trifluoro-2-chloroethane obtained from step C together with hydrogen fluoride to said first reaction zone (step A), and wherein 1,1,2,2-tetrachloroethane is fed to the process.

Preferably trichloroethylene and 1,1,2,2-tetrachloroethane are co-fed to the above process. In this case, 1,1,2,2-tetrafluoroethane (HFA 134) will be a co-product of the process which can be separated out together with the 1,1,1,2-tetrafluoroethane (HFA 134a).

The invention is illustrated but not limited by the following examples.

EXAMPLE 1

2 liters of crystalline chromia were charged to an Inconel tube reactor of diameter 4", and the chromia was calcined by heating to 400° C. in a stream of air (300 ml/minute) for 16 hours. The calcined chromia was then pre-fluorinated by heating to 350° C. in a stream of hydrogen fluoride (1 liter/minute) until hydrogen fluoride was detected in the off gas from the reactor. Tetrachloroethane was then passed over the catalyst from a liquid reservoir via a trace-heated line to the bottom of the reactor at a flow rate of 300 ml/minute. Hydrogen fluoride was also passed over the catalyst by feed to the bottom of the reactor at a rate of 1.5 liter/minute. The ratio of hydrogen fluoride:1,1,2,2,-tetrachloroethane was maintained at 6:1. The temperature of the reactor was varied within the range 200° C. to 300° C. The reactor off-gases were sampled and analysed by gas chromatography; the results are shown in Table 1.

TABLE 1

| TEMP | OFF-GAS COMPOSITION. (% w/w) | | | | | | |
|---|---|---|---|---|---|---|---|
| (°C.) | 143a | 1122 | 125 | 134a | 134 | 124 | 133a |
| 239 | 0.5 | 0.3 | 1.0 | 11.3 | 23.3 | 2.1 | 51.5 |
| 245 | 0.5 | 0.3 | 1.9 | 10.3 | 19.0 | 1.6 | 55.0 |
| 258 | 0.6 | 0.4 | 2.1 | 11.5 | 16.1 | 1.9 | 58.6 |
| 279 | 5.2 | 2.8 | 4.4 | 20.5 | 24.6 | 0.8 | 34.6 |
| 295 | 7.1 | 4.2 | 5.8 | 17.4 | 23.9 | 1.7 | 32.2 |

EXAMPLES 2–4

In each of these Examples, hydrogen fluoride and 1,1,2,2-tetrachloroethane were vaporised by nitrogen sparging liquid feed reservoirs; diluent nitrogen accounted for 50–65% of the feed gas composition.

In all the cases the catalyst was dried for 16 hours under nitrogen at 300° C. and prefluorinated at 200°–300° C. with HF/nitrogen prior to use.

HF and 1,1,2,2-tetrachloroethane (sym-tetra) were fed to an Inconel tube reactor (0.3 cm internal diameter) containing 2 ml of catalyst. The reactor temperature was varied between 270°–350° C. The reactor off gas was sampled, scrubbed of HF by treatment with soda ash and analysed by GC.

EXAMPLE 2

Catalyst = 8% Zn/chromia*
HF:Sym-tetra feed ratio = 15.5:1
Feed rates:HF = 31 mls/min:Sym-tetra = 2 mls/min:
Nitrogen = 50 mls/min % GC Area Counts

| Temp | S-Tet | Tri | 131 | 132a | 133 | 133a | 134 | 134a | Others |
|---|---|---|---|---|---|---|---|---|---|
| 298 | 1.45 | 31.04 | 1.38 | 25.62 | 20.48 | 2.33 | 10.62 | (0.033) | 9.80 |
| 308 | 0.22 | 31.37 | 0.73 | 23.32 | 20.97 | 2.18 | 12.30 | — | 11.83 |
| 320 | 0.13 | 32.44 | 0.60 | 19.69 | 20.33 | 2.36 | 15.81 | — | 11.83 |
| 339 | 0.08 | 33.81 | 0.20 | 9.16 | 15.16 | 3.74 | 28.44 | — | 13.29 |

EXAMPLE 3

Catalyst = 8% Zn/chromia
HF:Sym-tetra feed ratio = 10:1
Feed rates:HF = 31 mls/min:Sym-tetra = 2 mls/min:
Nitrogen = 27 mls/min % GC Area Counts

| Temp | S-Tet | Tri | 131 | 132a | 133 | 133a | 134 | 134a | Others |
|---|---|---|---|---|---|---|---|---|---|
| 270 | 1.1 | 3.2 | 0.48 | 10.12 | 12.98 | 28.7 | 19.7 | 0.5 | 22.4 |
| 290 | 0.92 | 2.9 | 0.1 | 4.0 | 8.0 | 36.2 | 34.5 | 1.1 | 12.3 |
| 310 | 1.1 | 1.2 | 0 | 1.0 | 3.3 | 35.8 | 39.2 | 2.0 | 16.4 |
| 330 | 0.2 | 0.6 | 0 | 0.5 | 2.8 | 36.5 | 42.24 | 3.3 | 13.9 |

*Prepared by co-precipitation of zinc and chromium hydroxides as described in EP 502605

EXAMPLE 4

Catalyst = Chromia
HF:Sym-tetra feed ratio = 10:1
Feed rates:HF = 20 mls/min:Sym-tetra = 2 mls/min:
Nitrogen = 27 mls/min

| Temp | 134/a | 133a | 133 | 132a | TRI | S-Tet | Others |
|---|---|---|---|---|---|---|---|
| 270 | 10.9 | 49.0 | 18.2 | 14.1 | 5.9 | 0.1 | 1.8 |
| 292 | 31.7 | 58.1 | 5.5 | 2.1 | 1.6 | 0.1 | 0.9 |
| 310 | 38.6 | 57.3 | 2.2 | 0.5 | 0.3 | 0.1 | 1.0 |
| 332 | 36.3 | 58.8 | 2.3 | 0.5 | 0.2 | 0.1 | 1.8 |
| 350 | 36.0* | 60.0 | 1.8 | 0.4 | 0.2 | 0.1 | 1.5 |

*this total 134/134a comprises 10.5% 134a and 25.4% 134 at 350° C. [134/a denotes a mixture of 134 and 134a]

EXAMPLES 5 AND 6

The procedures described in Examples 2-4 were followed but using 50 ml of the catalyst in an Inconel tube reactor i=of internal diameter 2.5 cm and length 10 cm to provide a longer contact time within the reactor.

EXAMPLE 5

Catalyst = 8% Zn/chromia
HF:Sym-tetra feed ratio = 10:1
Feed rates:HF = 20 mls/min:Sym-tetra = 2 mls/min:
Nitrogen = 27 mls/min

| Temp | S-Tet | Tri | 132a | 133 | 133a | 134/a | 134a | Others |
|---|---|---|---|---|---|---|---|---|
| 269 | 0.3 | 7.6 | 5.8 | 11.3 | 33.5 | 39.6 | — | 1.9 |
| 291 | 0.3 | 1.3 | 0.9 | 3.2 | 39.6 | 53.8 | — | 0.9 |
| 310 | 0.3 | 0.3 | 0.9 | 3.3 | 42.2 | 52.0 | — | 1.0 |
| 329 | 0.2 | 0.2 | 1.3 | 4.1 | 45.4 | 47.2* | — | 1.6 |

*this total 134 + 134a comprises 42.5% 134 and 4.7% 134a at 329° C.

EXAMPLE 6

Catalyst = 8% Zn/chromia
HF:Sym-tetra feed ratio = 10:1
Feed rates:HF = 20 mls/min:Sym-tetra = 2 mls/min:
Nitrogen - varied between 20 mls/min to 120 mls/min

| Temp | N2 Flow mls/min | Tri | 133 | 133a | 134/a | Others |
|---|---|---|---|---|---|---|
| 350 | 20 | 0.2 | 3.0 | 41.9 | 51.3 | 3.6 |
| 350 | 70 | 0.5 | 2.6 | 39.7 | 53.8 | 3.4 |
| 350 | 120 | 1.0 | 2.4 | 39.1 | 54.9 | 2.6 |

EXAMPLES 7 AND 8

1,1,2,2-tetrachloroethane (5 mmol) was added dropwise to an ice cooled FEP flask containing 5 mol % solution of metal fluoride in HF containing 40 mmol of $TiF_4$ (Example 10), or 35 mmol of $SbF_5$. The resulting mixture was stirred at room temperature for 30 minutes after which a gas sample was taken from the headspace, washed with water and analysed by gas chromatography.

| | *S-Tet | Tri | 131 | 132a | 133 | 133a | 134 | 134a | 1121 | Others |
|---|---|---|---|---|---|---|---|---|---|---|
| Ex 7 | 0.85 | 0.35 | — | 1.85 | 29.88 | 46.69 | 15.18 | — | trace | 2.2 |
| Ex 8 | 50.14 | 0.12 | 7.52 | 7.84 | 14.62 | 15.98 | 1.82 | — | trace | 1.96 |

*1,1,2,2-tetrachloroethane

We claim:

1. A process for the production of 1,1,2,2-tetrafluoroethane which comprises contacting 1,1,2,2-tetrachloroethane with hydrogen fluoride in the vapour phase at a temperature in the range of about 200° C. to about 400° C. in the presence of a chromia based fluorination catalyst, the 1,1,2,2-tetrachloroethane being kept at a temperature below the reaction temperature before said contact and being vaporized for the reaction just prior to said contact in order to minimize the decomposition of 1,1,2,2-tetrachloroethane to trichloroethylene.

2. A process as claimed in claim 1 which includes the additional step of isomerizing the 1,1,2,2-tetrafluoroethane to 1,1,1,2-tetrafluoroethane.

3. A process as claimed in claim 1 wherein the hydrogen fluoride is present in stoichiometric excess with respect to the 1,1,2,2-tetrachloroethane.

4. A process as claimed in claim 1, 2 or 3 wherein the relative proportion of hydrogen fluoride to 1,1,2,2,-tetrachloroethane is from 4:1 to 50:1.

5. A process as claimed in any one of claims 1 to 3 which is a vapour-phase process wherein the temperature is from 200° C. to 350° C.

6. A process as claimed in claim 1 wherein the fluorination catalyst is a zinc promoted chromia catalyst.

7. A vapour-phase process as claimed in claim 1 wherein 1,1,2,2-tetrachloroethane and trichloroethylene are co-fed as starting materials.

8. A process as claimed in claim 7 which comprises (A) contacting a mixture of 2-chloro-1,1,1-trifluoroethane and hydrogen fluoride with a fluorination catalyst at a temperature in the range from about 280° C. to about 450° C. in a first reaction zone to form a product containing 1,1,1,2-tetrafluoroethane and hydrogen chloride together with unreacted starting materials, (B) passing product of step (A) together with trichloroethylene and 1,1,2,2-tetrachloroethane to a second reaction zone containing a fluorination catalyst at a temperature in the range from about 200° C. to about 400° C. but lower than the temperature in step (A) to form a product containing 2-chloro-1,1,1-trifluoroethane, 1,1,1,2-tetrafluoroethane, hydrogen chloride and unreacted starting materials, (C) treating product of step (B) to separate 1,1,1,2-tetrafluoroethane and hydrogen chloride from 2-chloro-1,1,1-trifluoroethane, and unreacted starting materials, and (D) feeding 2-chloro-1,1,1-trifluoroethane obtained from step (C) together with hydrogen fluoride to said first reaction zone (step A)

wherein 1,1,2,2-tetrachloroethane is fed to the process and partially fluorinated derivatives of the 1,1,2,2-tetrachloroethane are fed with the 2-chloro-1,1,1-trifluoroethane in step (D).

9. A process as claimed in claim 8 wherein the 1,1,2,2-tetrachloroethane is co-fed with the trichloroethylene in step (B).

10. A process for the production of 1,1,2,2-tetrafluoroethane and 1,1,1,2-tetrafluoroethane which comprises contacting 1,1,2,2-tetrachloroethane with hydrogen fluoride in the vapor phase in the presence of a zinc promoted chromia catalyst and at a temperature of 250° C.–350° C., the 1,1,2,2-tetrachloroethane being kept at a temperature below the reaction temperature before said contact and being vaporized for reaction just prior to said contact in order to minimize decomposition of the 1,1,2,2-tetrachloroethane to trichloroethylene.

* * * * *